United States Patent
Darmstadt et al.

(10) Patent No.: US 9,804,149 B2
(45) Date of Patent: Oct. 31, 2017

(54) PATIENT-BASED RESULTS DISPLAY

(71) Applicant: Bio-Rad Laboratories, Inc., Hercules, CA (US)

(72) Inventors: Adam Darmstadt, Hercules, CA (US); Michael Waite, Hercules, CA (US); Theresa Forni, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 430 days.

(21) Appl. No.: 14/048,305

(22) Filed: Oct. 8, 2013

(65) Prior Publication Data

US 2014/0100791 A1 Apr. 10, 2014

Related U.S. Application Data

(60) Provisional application No. 61/712,164, filed on Oct. 10, 2012.

(51) Int. Cl.
| | |
|---|---|
| *G01N 33/49* | (2006.01) |
| *G01N 35/00* | (2006.01) |
| *G06F 19/00* | (2011.01) |

(52) U.S. Cl.
CPC ....... *G01N 33/49* (2013.01); *G01N 35/00603* (2013.01); *G01N 35/00732* (2013.01); *G06F 19/366* (2013.01); *G01N 2035/00831* (2013.01)

(58) Field of Classification Search
USPC ................................. 600/347, 368
See application file for complete search history.

(56) References Cited

U.S. PATENT DOCUMENTS

| | | | |
|---|---|---|---|
| 5,284,623 A | 2/1994 | Yamori et al. | |
| 7,996,172 B2 | 8/2011 | Bauer et al. | |
| 2004/0030586 A1 | 2/2004 | Cucchiara et al. | |
| 2005/0131734 A1* | 6/2005 | Sugiyama | G06F 19/366 705/2 |

(Continued)

OTHER PUBLICATIONS

International Search Report and Written Opinion of related PCT Application No. PCT/US2013/064062 dated Dec. 13, 2013, 17 pages.

(Continued)

*Primary Examiner* — Elaine Gort
*Assistant Examiner* — Rajiv Raj
(74) *Attorney, Agent, or Firm* — Kilpatrick Townsend & Stockton LLP

(57) ABSTRACT

A medical testing machine provides improved recall and display of the outcomes of tests performed by the machine. Test outcomes and other information are stored in mass storage directly accessible by the medical testing machine. In one aspect, outcomes of tests relating to a particular patient may be recalled. The system may be especially useful for tests that may be performed multiple times for a particular patient over a period of time, for example testing for HbA1c hemoglobin levels in diabetes patients. According to another aspect, the medical testing machine may store an accession number for each test outcome, and may enable a user to display as a group test outcomes having the same accession number. The system may store further information and associate it with particular test outcomes, for example calibration information. The system may also store a set of rules under which each test instance was run.

28 Claims, 12 Drawing Sheets

(56) References Cited

U.S. PATENT DOCUMENTS

| | | | |
|---|---|---|---|
| 2006/0180659 A1* | 8/2006 | Loffredo | G06F 3/1205 235/380 |
| 2007/0037144 A1 | 2/2007 | Wohlgemuth et al. | |
| 2007/0047392 A1* | 3/2007 | Parkinson | G04F 1/005 368/108 |
| 2007/0231846 A1 | 10/2007 | Cosentino et al. | |
| 2007/0269804 A1 | 11/2007 | Liew et al. | |
| 2008/0026485 A1 | 1/2008 | Hueber et al. | |
| 2009/0041800 A1* | 2/2009 | Woiwode | A61K 9/08 424/195.15 |
| 2009/0318775 A1 | 12/2009 | Michelson et al. | |
| 2009/0325299 A1* | 12/2009 | Hamada | G01N 35/026 436/55 |
| 2010/0324874 A9* | 12/2010 | Bangs | G06F 19/3437 703/11 |
| 2011/0195508 A1 | 8/2011 | Selinfreund et al. | |
| 2011/0312683 A1* | 12/2011 | Silverbrook | B01L 3/5027 506/39 |
| 2012/0251495 A1* | 10/2012 | Moheno | A61K 31/505 424/85.7 |
| 2013/0132897 A1 | 5/2013 | Schultz et al. | |
| 2013/0200140 A1* | 8/2013 | Kawabata | A61B 5/14532 235/375 |

OTHER PUBLICATIONS

International Preliminary Report on Patentability dated Apr. 23, 2015 in PCT Patent Application No. PCT/US2013/064062. 9 pages.
Examination Report No. 1 dated Dec. 17, 2015 in AU Patent Application No. 2013329349. 3 pages.
Office Action dated Apr. 25, 2016 in CA Patent Application No. 2,887,552. 4 pages.
Extended European Search Report dated May 3, 2016 in EP Patent Application No. 13844784.2. 8 pages.
Examination Report No. 2 dated Jun. 30, 2016 in AU Patent Application No. 2013329349. 4 pages.
Examination Report No. 3 dated Oct. 26, 2016 in AU Patent Application No. 2013329349. 3 pages.
First Office Action dated Nov. 30, 2016 in CN Patent Application No. 201380064030.2. with English translation. 34 pages.
Office Action dated Jun. 19, 2017 in CA Patent Application No. 2,887,552. 3 pages.
Office Action dated Aug. 2, 2017 in CN Patent Application No. 201380064030.2, with partial English translation. 18 pages.

* cited by examiner

400

| HOME | RESULTS | QC | CALIB | UTILITIES | SETTINGS |

All  🏳  ★  ☰   Custom Filter

Show Results Matching

Type:
■ Patient
■ Patient-Stat
■ QC
■ Calibrator

Status:
■ Released
■ Held
■ Rejected

Flagged:
■ Not flagged
■ Flagged
● Any reason
○ Flagged for QC

Saved Filters:
| All |
| Flagged |
| Favorite |

☐ Time Int.
● Since: [8:00 AM ▼]  [Today ▼]
○ Most recent  [8]  ● Hours  ○ Days
○ From: [3/12/2012 ▼] [8:00 AM ▼]  To: [3/17/2012 ▼] [8:00 AM ▼]

■ Patient ID
Accession no. [              ]  ☐ Match exactly
Patient Name: Last: [    ]  First: [    ]  ☐ Match exactly
Patient ID: [33333]  ☐ Match exactly
Date of Birth: [    ▼]

401

☐ Comment text [                    ]  ☐ Match exactly

☐ Result Values
A1c: [Greater than ▼] [    ] [% ▼]
Peak: [    ▼] [Greater than ▼] [    ] [% ▼]

[ Save/Edit ]  [ Filter ]  [ Cancel ]

| HOME | RESULTS | QC | CALIB. | UTILITIES | SETTINGS |

All 🏳 ★ ▼   Custom Filter: Patient 33333       4 Rows (0 selected)

| ☐ | Date/Time | Accession #/ Position | | HbA1c | | Note/ Comment | Status |
|---|---|---|---|---|---|---|---|
| ☐ | 9/25/2012 11:06:42 AM | FH001235 Rack: 1 Position 3 | | 133 mmol/ mol | | | |
| ☐ | 6/18/2012 2:31:22 PM | FH001003 Rack: 8 Position 7 | ↻ | 125 mmol/ mol | 🏳 | Repeat test Area out of range | |
| ☐ | 6/18/2012 2:20:05 PM | FH001003 Rack: 3 Position 5 | ↻ | | 🏳 | Repeat test Area out of range | |
| ☐ | 3/21/2012 10:17:48 AM | FH000802 Rack: 9 Position 3 | | 128 mmol/ mol | | | |

501 points to the third row; 502 points to the fourth row.

🚫 Reject    ↗ Release                                    🖨 Print

| | HOME | RESULTS | QC | CALIB | UTILITIES | SETTINGS |

All  Custom Filter: Patient 124<HbA1c<131    8 Rows (0 selected)

| | Date/Time | Accession #/ Position | 704 | HbA1c | Note/ Comment | Status |
|---|---|---|---|---|---|---|
| ☐ | 6/18/2012 3:53:42 PM | FH001005 Rack: 8 Position 9 | | 130 mmol/ mol | | |
| ☐ | 6/18/2012 2:31:22 PM | FH001003 Rack: 8 Position 7 | ↻ | 125 mmol/ mol | Repeat test Area out of range | |
| ☐ | 6/18/2012 1:13:45 PM | FH001001 Rack: 8 Position 5 | | 127 mmol/ mol | | |
| ☐ | 6/18/2012 1:09:48 PM | FH000997 Rack: 8 Position 1 | | 128 mmol/ mol | | |
| ☐ | 6/18/2012 12:44:42 PM | FH000996 Rack: 7 Position 10 | | 130 mmol/ mol | | |
| ☐ | 6/18/2012 12:21:22 PM | FH000993 Rack: 7 Position 7 | ↻ | 125 mmol/ mol | Repeat test Area out of range | |
| ☐ | 6/18/2012 11:53:05 AM | FH000991 Rack: 7 Position 5 | | 129 mmol/ mol | | |
| ☐ | 6/18/2012 10:17:48 AM | FH000990 Rack: 7 Position 4 | | 128 mmol/ mol | | |

701 points to rows 2-3; 702 points to row 6; 703 labeled below table.

Reject    Release    Print

| | HOME | RESULTS | QC | CALIB | UTILITIES | SETTINGS |

All 🏳 ★ ▼  Custom Filter: Patient 124<HbA1c<131   8 Rows (0 selected)

| ☐ | Date/Time | Accession #/ Position | | HbA1c | Note/ Comment | Status |
|---|---|---|---|---|---|---|
| ☐ | 6/18/2012 12:22:12 PM | FH000993 Rack: 7 Position 8 | ②↻ | 123 mmol/mol | | |
| ☐ | 6/18/2012 12:21:22 PM | FH000993 Rack: 7 Position 7 | ①↻ | 125 mmol/mol | 🏳 Repeat test Area out of range | |
| ☐ | 6/18/2012 12:20:07 PM | FH000993 Rack: 7 Position 6 | ↻ | 122 mmol/mol | | |
| ☐ | 6/18/2012 11:53:05 AM | FH000991 Rack: 7 Position 5 | | 129 mmol/mol | | |
| ☐ | 6/18/2012 10:17:48 AM | FH000990 Rack: 7 Position 4 | | 128 mmol/mol | | |
| ☐ | 6/18/2012 10:00:05 AM | FH000987 Rack: 7 Position 1 | | 129 mmol/mol | | |
| ☐ | 6/18/2012 9:37:48 AM | FH000982 Rack: 6 Position 6 | | 128 mmol/mol | | |
| ☐ | 6/18/2012 9:18:05 AM | FH000980 Rack: 6 Position 4 | | 129 mmol/mol | | |
| ☐ | 6/18/2012 8:55:48 AM | FH000975 Rack: 5 Position 9 | | 128 mmol/mol | | |

🚫 Reject   ↗ Release                                    🖨 Print

802 — (row 2)
702 — (row 3)
801 — (row 4)

| | HOME | RESULTS | QC | CALIB | UTILITIES | SETTINGS |

All 🏳 ★ ☰   Custom Filter: Patient 124<HbA1c<131   8 Rows (0 selected)

| ☐ | Date/Time | Accession #/ Position | | HbA1c | Note/ Comment | Status |
|---|---|---|---|---|---|---|
| ☐ | 6/18/2012 2:31:22 PM | FH001003 Rack: 8 Position 7 | ↻ | 125 mmol/ mol | 🏳 Repeat test Area out of range | |
| ☐ | 6/18/2012 2:20:05 PM | FH001003 Rack: 3 Position 5 | ↻ | | 🏳 Repeat test Area out of range | |
| ☐ | 6/18/2012 1:13:45 PM | FH001001 Rack: 8 Position 5 | | 127 mmol/ mol | | |
| ☐ | 6/18/2012 1:09:48 PM | FH000997 Rack: 8 Position 1 | | 128 mmol/ mol | | |
| ☐ | 6/18/2012 12:44:42 PM | FH000996 Rack: 7 Position 10 | | 133 mmol/ mol | | |
| ☐ | 6/18/2012 12:21:22 PM | FH000993 Rack: 7 Position 7 | ↻ | 125 mmol/ mol | Repeat test Area out of range | |
| ☐ | 6/18/2012 11:53:05 AM | FH000991 Rack: 7 Position 5 | | 129 mmol/ mol | | |
| ☐ | 6/18/2012 10:17:48 AM | FH000990 Rack: 7 Position 4 | | 128 mmol/ mol | | |

701 — (points to first row)
502 — (points to second row)

🚫 Reject    ↗ Release                                             🖨 Print

FIG. 9

PATIENT-BASED RESULTS DISPLAY

CROSS-REFERENCE TO RELATED APPLICATIONS

This application claims the benefit of U.S. Provisional Patent Application No. 61/712,164 filed Oct. 10, 2012 and titled "Patient-Based Results Display", the entire disclosure of which is hereby incorporated by reference herein.

BACKGROUND OF THE INVENTION

In the diagnosis and monitoring of diseases, medical tests are often performed on blood, tissue, or other media sampled from patients. In a typical scenario, a doctor requests that a particular test be performed, and a sample is taken from the patient. The sample is sent to an on-site or off-site testing lab, and the results of the test are returned to the doctor for review and reporting to the patient. The test results are also typically placed in the patient's file.

Some conditions require ongoing monitoring. In these cases, tests may be performed multiple times for a particular patient.

BRIEF SUMMARY OF THE INVENTION

According to one aspect, a medical testing machine includes a testing system for performing a medical test on media sampled from patients. Each test instance has an outcome. The medical testing machine further includes a reader that obtains, for each of a plurality of test instances, an identifier of the particular patient from which the media was sampled. The medical testing machine further includes a processor that causes test outcomes to be stored in a mass storage memory in association with its respective patient identifier, and a computerized retrieval system. The computerized retrieval system enables a user to specify a particular patient identifier and cause the computerized retrieval system to retrieve from the data storage test outcomes associated with the particular patient identifier. In some embodiments, the reader obtains the identifier by reading it from a container that holds the media. In some embodiments, the media is blood, and the test measures the level of HbA1c hemoglobin in the blood. In some embodiments, the medical testing machine further comprises an electronic display on which the retrieved outcomes are shown. In some embodiments, the electronic display is a touchscreen display and also serves as an input device for receiving inputs from the user. In some embodiments, the medical testing machine comprises the mass storage memory. In some embodiments, the mass storage memory is remote from the medical testing machine and is accessible via a computer network. The reader may further obtain for each test instance an accession number of the respective sample. In some embodiments, the medical testing machine further comprises a user interface control that causes test outcomes having the same accession number to be shown in a group on the display. In some embodiments, the test outcomes having the same accession number are shown in the group on the electronic display regardless of whether one or more of the grouped test outcomes would otherwise be omitted from being shown on the electronic display by a data filter in place at the time the user interface control is actuated. The computerized retrieval system may enable multiple levels of detail to be shown about each test instance outcome. In some embodiments, the mass storage memory also stores in association with each test instance outcome information about the state of the medical testing machine at the time the particular test instance was run. The stored state information may include a set of rules used to evaluate test outcomes for validity. In some embodiments, the medical testing machine further comprises a user interface control that causes to be displayed, for a particular test instance, the rules in place at the time the particular test instance was run. In some embodiments, the medical testing machine further comprises an electronic display, wherein during a particular test instance, an animated counter counts down the time remaining until the test is completed. In some embodiments, the electronic display further shows a rack number and position within the rack of a container from which media was extracted for running the particular test instance. In some embodiments, the electronic display further shows levels of consumable materials remaining in the medical testing machine.

According to another aspect, a medical testing machine includes a testing system for performing a medical test on media sampled from patients. Each test instance has an outcome. The medical testing machine further includes a reader that obtains, for each of a plurality of test instances, an accession number of the particular media sample. The medical testing machine further includes a processor that causes each test outcome to be stored in a mass storage memory in association with its respective accession number, and a computerized retrieval system. The computerized retrieval system enables a user to specify a particular accession number and cause the computerized retrieval system to display as a group all of the stored test outcomes having the same accession number. In some embodiments, the media is blood, and the test measures the level of HbA1c hemoglobin in the blood. The reader may obtain the accession number by reading it from a container that holds the media. In some embodiments, the test outcomes having the same accession number are displayed as a group regardless of whether one or more of the grouped test outcomes would otherwise be omitted from being displayed by a data filter in place at the time the group display is requested. In some embodiments, the mass storage also stores in association with each test instance outcome information about the state of the medical testing machine at the time the particular test instance was run. In some embodiments, the stored state indication includes a set of rules used to evaluate test outcomes for validity. In some embodiments, the medical testing machine further comprises an electronic display, wherein during a particular test instance, an animated counter counts down the time remaining until the test is completed.

According to another aspect, a medical testing machine includes a testing system for performing a medical test on media sampled from patients. Each test instance has an outcome. The medical testing machine further includes a processor that causes test outcomes to be stored in a mass storage memory in association with their respective patient identifiers, and a computerized retrieval system. The computerized retrieval system enables a user to specify a particular filter criterion and cause the computerized retrieval system to retrieve from the mass storage memory test outcomes meeting the filter criterion. The mass storage memory also stores in association with each test instance outcome information about the state of the medical testing machine at the time the particular test instance was run. In some embodiments, the media is blood, and the test measures the level of HbA1c hemoglobin in the blood. In some embodiments, the stored state information includes a set of rules used to evaluate test outcomes for validity. In some embodiments, the medical testing machine further comprises a user interface control that causes to be displayed, for a particular test instance, the rules in place at the time the particular test instance was run.

According to another aspect, a method includes the steps of accessing, using a computerized system, an electronic library of test outcomes obtained from the performance of medical tests on media samples; identifying in the library one or more sets of the test outcomes in which each outcome in a respective set results from testing of the same respective media sample; and displaying as a group the outcomes in at least one set. In some embodiments, identifying one or more sets of the test outcomes in which each outcome in a respective set results from testing of the same respective media sample comprises identifying sets of test outcomes having a same accession number. In some embodiments, the test outcomes in a set are displayed as a group regardless of whether one or more of the grouped test outcomes would otherwise be omitted from being displayed by a data filter in place at the time the group display is requested. The test outcomes may result from a test that measures the level of HbA1c hemoglobin in blood. The library of test outcomes may be stored in a testing machine used to perform the medical test. In some embodiments, the library of test outcomes is stored separately from a testing machine used to perform the medical test.

BRIEF DESCRIPTION OF THE DRAWINGS

FIG. 4 shows an example user interface screen that may be presented on a display, enabling a user to specify criteria by which to recall stored test information in accordance with embodiments of the invention.

FIG. 5 illustrates a second user interface screen, in accordance with embodiments.

FIG. 7 shows a user interface screen with a listing of test outcomes, in accordance with embodiments of the invention.

FIG. 8 shows a display of related outcomes, in accordance with embodiments of the invention.

FIG. 9 shows another user interface screen in accordance with embodiments of the invention.

DETAILED DESCRIPTION OF THE INVENTION

Embodiments of the invention provide improved access to medical test results and documentation of the conditions under which tests were performed. These techniques may be especially applicable for tests that are performed repeatedly.

One example of a condition that requires ongoing monitoring and repeated testing is diabetes. Diabetes is a name given to a class of conditions in which a patient exhibits elevated blood sugar levels, either because the patient's body does not produce enough of the metabolism-regulating hormone insulin, or because cells in the patient's body do not respond properly to insulin. Diabetes is increasingly prevalent in the United States and other parts of the world.

The management of diabetes often involves frequent blood sugar measurements, and many patients use at-home blood sugar testing devices to take frequent instantaneous readings of their blood sugar levels.

The patient's average blood glucose level over long periods of time, typically several months, is also reflected in the level of HbA1c hemoglobin in the patient's blood. Testing for HbA1c levels is more complex than testing for an instantaneous blood sugar level, and can be done using high performance liquid chromatography (HPLC) in a specialized testing machine. A patient may be tested several times per year and the resulting measured levels of HbA1c used as a check on how well the patient's blood sugar levels are being controlled.

Because a particular patient may visit the same doctor or clinic many times, the same testing machine may be used to test blood from the patient over the course of many months or years. Previously, this information was reported to the doctor and placed in the patient's medical record. Obtaining a time history of test results from the patient's medical record may be time consuming and error-prone.

In some cases, it may be desirable to correlate a particular test result with the conditions under which the test was run. For example, it may be desired for a particular test to know how recently the testing machine was calibrated before the test was run, a batch number for consumables used in the test, and other information. Previously, such a correlation would require searching calibration logs and other records maintained by the testing facility, and correlating them with patient records.

In embodiments of the invention, the testing machine itself stores detailed records of tests, and enables retrieving test results by patient identification number and other parameters. The testing machine may also record maintenance and calibration information, consumable item serial numbers, and other information that enables efficient correlation of test conditions with patient test results.

Figure 1:
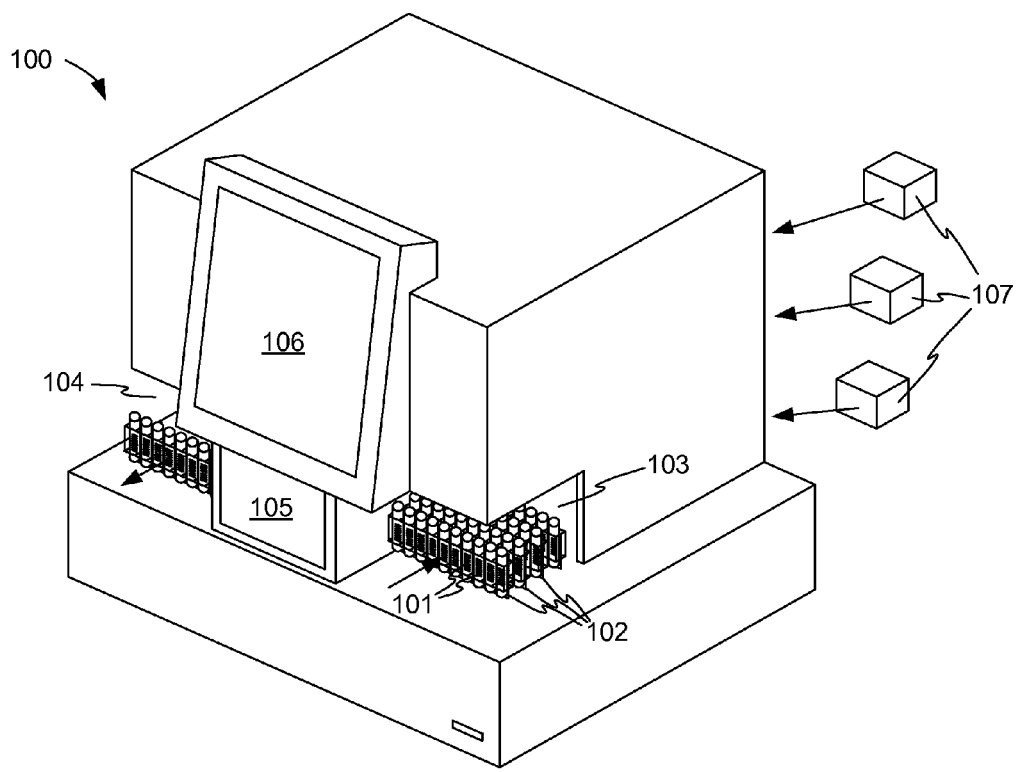
FIG. 1 shows a medical testing machine in accordance with example embodiments of the invention.

FIG. 1 shows a medical testing machine 100 in accordance with example embodiments of the invention. While testing machine 100 is configured for testing blood samples for the level of HbA1c hemoglobin, it will be understood that the principles of the invention are applicable to testing machines used for other purposes as well. Vials 101 containing blood sampled from patients are loaded into racks 102, which are then placed into testing machine 100 at input location 103. Vials 101 are examples of containers for patient media, but in other kinds of tests, other kinds of containers may be used. An automated testing system within medical testing machine 100 extracts a quantity from each vial in sequence, and for each sample performs HPLC to determine the level of HbA1c in the blood. When all of the vials in a rack have been tested, the rack is delivered out of the machine at output location 104. A "STAT input" 105 may be provided for initiating an out-of-sequence test. Placing a vial in stat drawer 105 causes the vial to be tested immediately, without having to wait for the vials previously placed at input location 103 to be processed.

Test results and other information are shown on a display screen 106, as is described in more detail below. Display screen 106 may be any suitable type of display, for example a flat panel liquid crystal display (LCD). Display screen 106 may also include a touchscreen, and serve as an input device for receiving inputs from the user of medical testing machine 100.

HPLC by its nature uses certain consumable materials, for example buffers and washing solution, and packets 107 of consumable materials may be periodically replaced in medical testing machine 100. The stationary media used in HPLC may also be periodically replaced.

Figure 2:
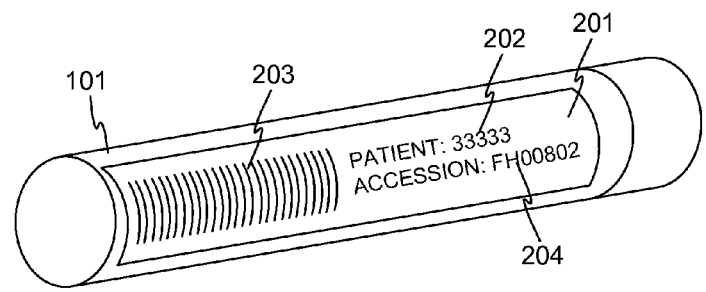
FIG. 2 shows a vial as may be used in the medical testing machine of FIG. 1, in more detail.

FIG. 2 shows a vial 101 in more detail. Each vial 101 is labeled with a machine-readable label 201 carrying information about the sample. Many different label formats are possible. Example label 201 includes a patient identifier 202, which may be shown in human-readable form as well as in machine readable form such as in barcode 203. Label 201 may also include an accession number 204. For the purposes of this disclosure, an accession number is any numeric, alphabetic, alphanumeric, symbolic, or other identifier unique to a particular media sample. Example accession number 204 is an identifier unique to the particular media in vial 101. In some cases, multiple vials 101 may have the same accession number, as is explained in more detail below. Accession number 204 is also preferably shown in machine readable form such as in barcode 203. Because a particular patient may visit the facility where medical testing machine 100 is used multiple times (or multiple samples from the patient may be sent to the facility), over a period of time multiple vials 101 may be labeled with the same patient number, but have unique accession numbers. In some cases, the sample in a particular vial may be tested more than once, as will be explained in more detail below.

Figure 3:
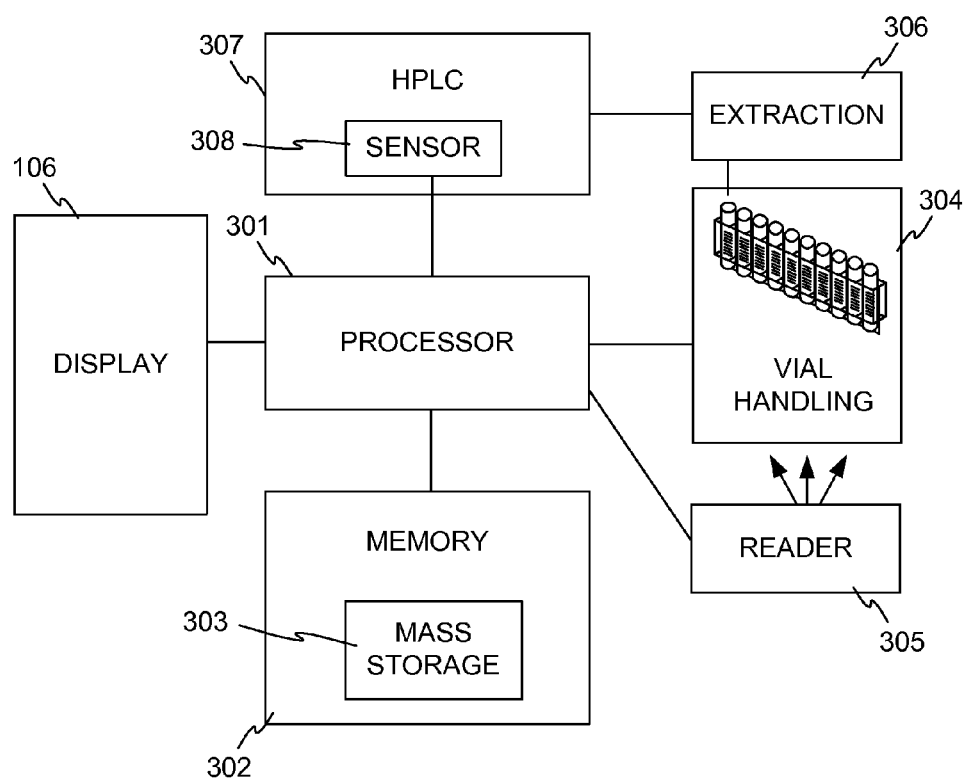
FIG. 3 shows a simplified block diagram of the architecture of the medical testing machine of FIG. 1, in accordance with embodiments of the invention.

FIG. 3 shows a simplified block diagram of the architecture of medical testing machine 100, in accordance with embodiments of the invention. A processor 301 generally controls the operation of medical testing machine 100. Processor 301 may be any suitable kind of microprocessor, microcontroller, digital signal processor, or other circuitry capable of performing the required functions. Memory 302 may include different kinds of memory, alone or in combination, and stores a variety of digital information. For example, memory 302 may include random access memory (RAM), read only memory (ROM), re-writable non-volatile memory such as flash memory, other kinds of memory, or any suitable combination thereof. In particular, memory 302 includes mass storage 303 for non-volatile storage of large quantities of information, for example the results of tests performed by medical testing machine 100. Mass storage 303 may include magnetic disk storage, optical disk storage, solid state memory, other kinds of storage, or any suitable combination thereof.

Memory 302 preferably holds instructions that, when executed by processor 301, cause medical testing machine 100 to perform its intended functions.

Medical testing machine 100 includes a vial handling mechanism 304, for moving vials of patient samples through the system for testing. A vial reader 305 reads information from vials 101. For example, vial reader 305 may be a barcode reader that reads bar coded information such as patient and accession numbers 202 and 204 from a label such as label 201. In other embodiments, a different mechanism may be provided for obtaining information about a sample, for example a radio frequency identification (RFID) scanner, optical character recognition, or another suitable mechanism. In some embodiments, a user may enter information manually.

An extraction mechanism 306 automatically, under control of processor 301, extracts blood from each vial in turn for testing, and delivers the samples to high performance liquid chromatography (HPLC) system 307. In general, liquid chromatography involves introducing a small quantity of the sampled blood into the flow of a liquid medium, and passing the liquid medium through a stationary medium. Different components of the introduced blood will traverse the stationary medium at different speeds, due to their different interactions with the liquid and stationary media. The stationary medium is sometimes referred to as a "column", although the stationary medium may not be arranged vertically. After a time, different components of the introduced blood sample will become separated within the column, and the separated components will arrive at the end of the column at different times. A sensor 308 near the end of the column watches for indications that the different components are passing. The indications may be differences in color, refractive index, spectral absorption characteristics, pH, or other characteristics. A brief overview of chromatography is given in co-pending U.S. Provisional Patent Application No. 61/559,399, the entire disclosure of which is hereby incorporated by reference herein.

The output of sensor 308 passes to processor 301, which determines the result of the test. Results may be shown on display screen 106. Test results are stored in mass storage 303, in association with other information such as the information read from the vial labels. In particular, a particular test result is stored in association with the patient identifier of the patient from which the tested media was sampled. Other kinds of information that are preferably included in the test information include the raw sensor output from the test, the time and result of the most recent calibration of medical testing machine 100, serial numbers or other identifying information about the consumable items used in the test, and any retest rules that were in place at the time of the test. Other kinds of information may also be stored. For example, as is explained in more detail below, a particular test may not produce a numerical result, because of a problem with the sample or an irregularity in the particular test. In this situation, the outcome of the test may be that there is no numerical result to report. For the purposes of this disclosure, the term "outcome" encompasses test outcomes with or without numerical results.

While mass storage 303 is depicted in FIG. 3 as being internal to medical testing machine 100, other arrangements are possible, and it is intended that the appended claims encompass other arrangements. For example, mass storage 303 may be external to medical testing machine 100 and connected to medical testing machine 100 by a cable or wireless interface. In some embodiments, mass storage 303 may be in a different location than medical testing machine 100 and connected to medical testing machine 100 through a computer network.

Over time, a particular testing machine 100 may perform many thousands of individual tests, accumulating the test outcomes in mass storage 303. Some patients may undergo multiple tests, so that the accumulated library of data in mass storage 303 will include instances where multiple tests have the same patient identifiers. This collection of information enables a user to conveniently and quickly produce reports that have previously been difficult to produce.

For example, testing machine 100 may enable retrieval of test results and other information according to one or more filters. FIG. 4 shows an example user interface screen 400 that may be presented on display screen 106, enabling a user to specify criteria by which to recall stored test information.

Among the criteria that may be used to retrieve stored test data is the patient identifier, as specified in area 401 of screen 400. In this example, the patient can be identified by a patient ID number such as may be assigned by a particular health care facility, by name, by date of birth, or by other information or combination of information. The retrieval of results and other information is preferably performed under the control of processor 301, and is thus performed by a computerized retrieval system.

In the example of FIG. 4, a user has entered a patient ID number. Once the user indicates that the information is to be retrieved, for example by touching the "Apply Filter" location on user interface screen 400, a second user interface screen may be shown.

FIG. 5 illustrates a second user interface screen 500, in accordance with embodiments. Screen 500 shows four test results that have been retrieved relating to patient 33333. In this example, patient 33333 has visited the clinic three times in the span of about six months. On the patient's second visit, the first attempt at testing the patient's blood sample was judged to be possibly erroneous, and the sample was tested a second time. Repeated tests are discussed in more detail below. The report shown in user interface screen 500 has been produced by medical testing machine 100, using data stored by and accessible to medical testing machine 100, and is thus produced quickly and efficiently.

In some embodiments, additional detail about each test instance is stored, and can be retrieved for more detailed analysis. For example, a user may indicate that a more detailed report is desired for one of the test instances listed in FIG. 5. The indication may be done in any suitable way, such as touching or tapping twice on display screen 106 over the displayed record.

Figure 6:
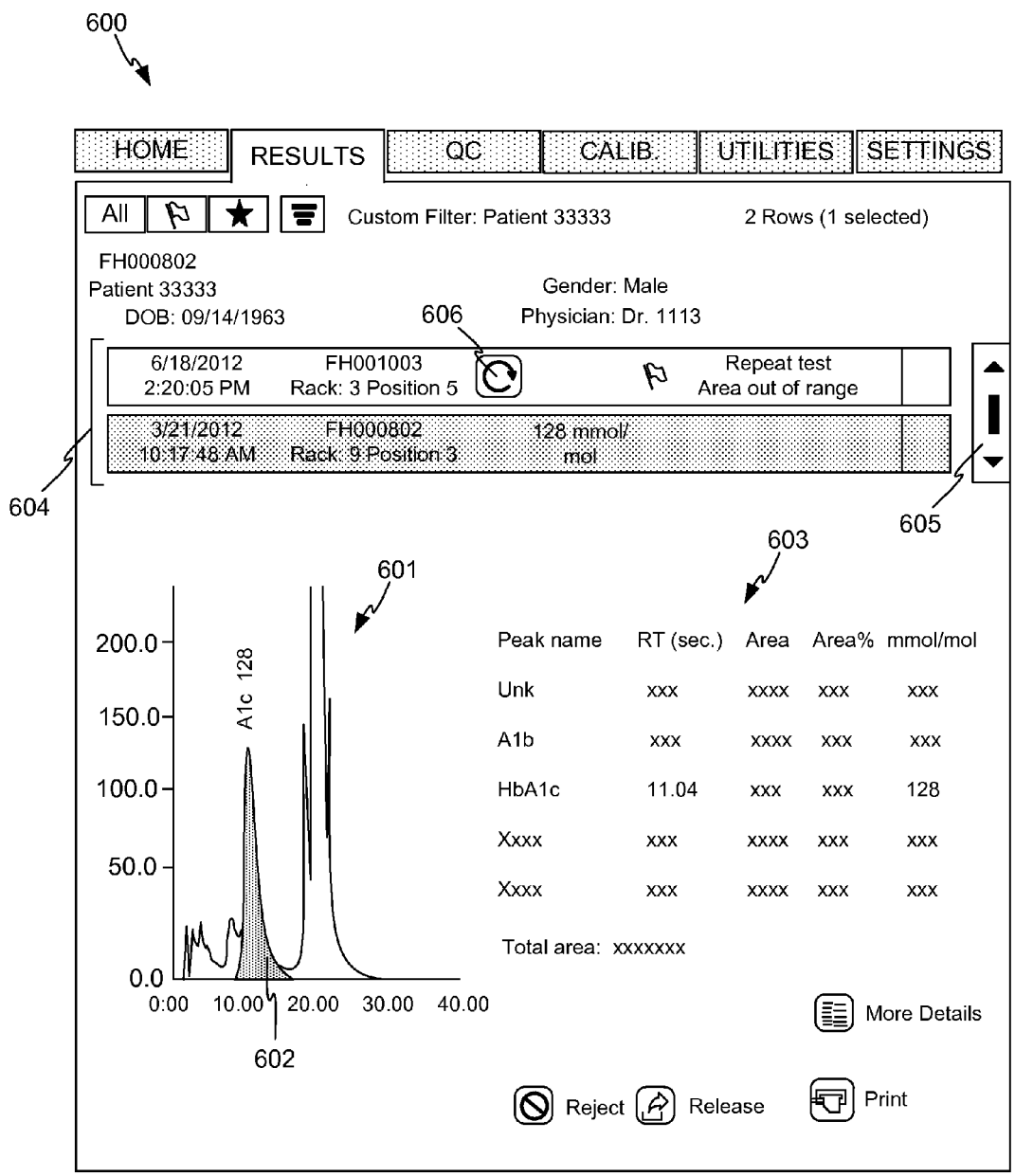
FIG. 6 shows an example embodiment of a more detailed report screen.

FIG. 6 shows an example of a more detailed report screen 600. The detailed report screen may include such information as a chromatogram 601 of the output of sensor 308. In FIG. 6, a peak 602 identified as representing HbA1c in the patient's blood has been highlighted in chromatogram 601. Tabular information 603 may also be presented, showing peaks identified in the output of sensor 308, and the corresponding blood components if known. Many other kinds of information could be presented.

In example report screen 600, the results presented in user interface screen 500 are also shown, but may be in a condensed format 604. In this example, only two tests from interface screen 500 are shown at a time, but the complete listing is accessible using a scrolling bar 605 or other suitable control, such as navigation buttons.

According to another aspect, embodiments of the invention facilitate display and investigation of repeated tests. In this context, a repeated test occurs when the same sampling of patient media is tested more than once. Repeated tests can occur for any of a variety of reasons. For example, at the time a patient's blood is drawn, the phlebotomist may draw more than one vial of blood, in anticipation that more than one vial will be needed to supply all of the tests ordered for the patient. All of the vials will be labeled with the same patient identifier and/or accession number. Even though only one vial may be needed for a particular test, more than one vial may be inadvertently placed in testing machine 100, resulting in multiple test results having the same patient identifier and accession number. After the first, any subsequent test results will be marked as repeated results. Preferably, the first result will also be marked as having been repeated, as is illustrated by icon 606 shown in FIG. 6. In another example, repeated tests can occur even if only one vial of blood is drawn. One way this can occur is that the first test on the vial is irregular in some way. Testing machine 100 may be programmed with a set of rules by which test results are evaluated for validity or other purposes. The rules may reflect expected characteristics of the particular test being evaluated. In one example, testing machine 100 may expect that the area under the curve of peak 602 will fall within a certain range. If the area measured in a particular test falls outside the expected range, testing machine 100 may automatically repeat the test, on the assumption that some problem occurred during the test that could be corrected by a retest. For example, if extraction mechanism 306 failed to extract sufficient blood from a particular vial, resulting in a low area for peak 602, a re-test may be successful in extracting a better sample. In other cases, a technician operating testing machine 100 may cause a vial to be retested.

The results of repeated test may be of particular interest, in evaluating a patient's testing history, in verifying proper testing machine functioning, and for other purposes. According to embodiments, testing machine 100 provides the capability to group sets of repeated tests for display and investigation.

FIG. 7 shows a user interface screen 700 with a listing of test results, in accordance with embodiments of the invention. In this example, the presented list has been filtered to show only results having HbA1c readings within a narrow range, but embodiments of the invention may work with lists filtered in any other way or not filtered at all. Thus, the example list of FIG. 7 shows results from any different patients and many different vials. Some of the tests shown in the list are repeats of earlier tests, but the related tests may not necessarily show in the list if their results do not meet the current filter criteria. For example, test 701 in FIG. 7 is recognizable as repeat test 501 shown in FIG. 5, but the corresponding test 502 does not appear in FIG. 7, because test 502 did not fit the filter criteria used to generate the list in FIG. 7. Another repeat test 702 also shows in FIG. 7.

A user of testing machine 100 may wish to investigate the circumstances of the repeat tests in more detail. By pressing icon 703, the user can cause all of the related tests to be displayed, as shown in user interface screen 800 of FIG. 8. Other kinds of user interface controls for causing a display of related repeat tests may be used as well.

In FIG. 8, test result 702 and its related tests 801 and 802 have been snapped to the top of the displayed list and highlighted to emphasize that they are related repeat tests. This view reveals that test 702 was a repeat of test 801, and was again repeated in test 802, and that the three tests all have the same accession number. This indicates that three vials from the same blood draw were placed into testing machine 100, likely unnecessarily. The HbA1c readings are very similar for all three, but two of the tests fell below the screening level used to generate the list in FIG. 7.

Figure 10:
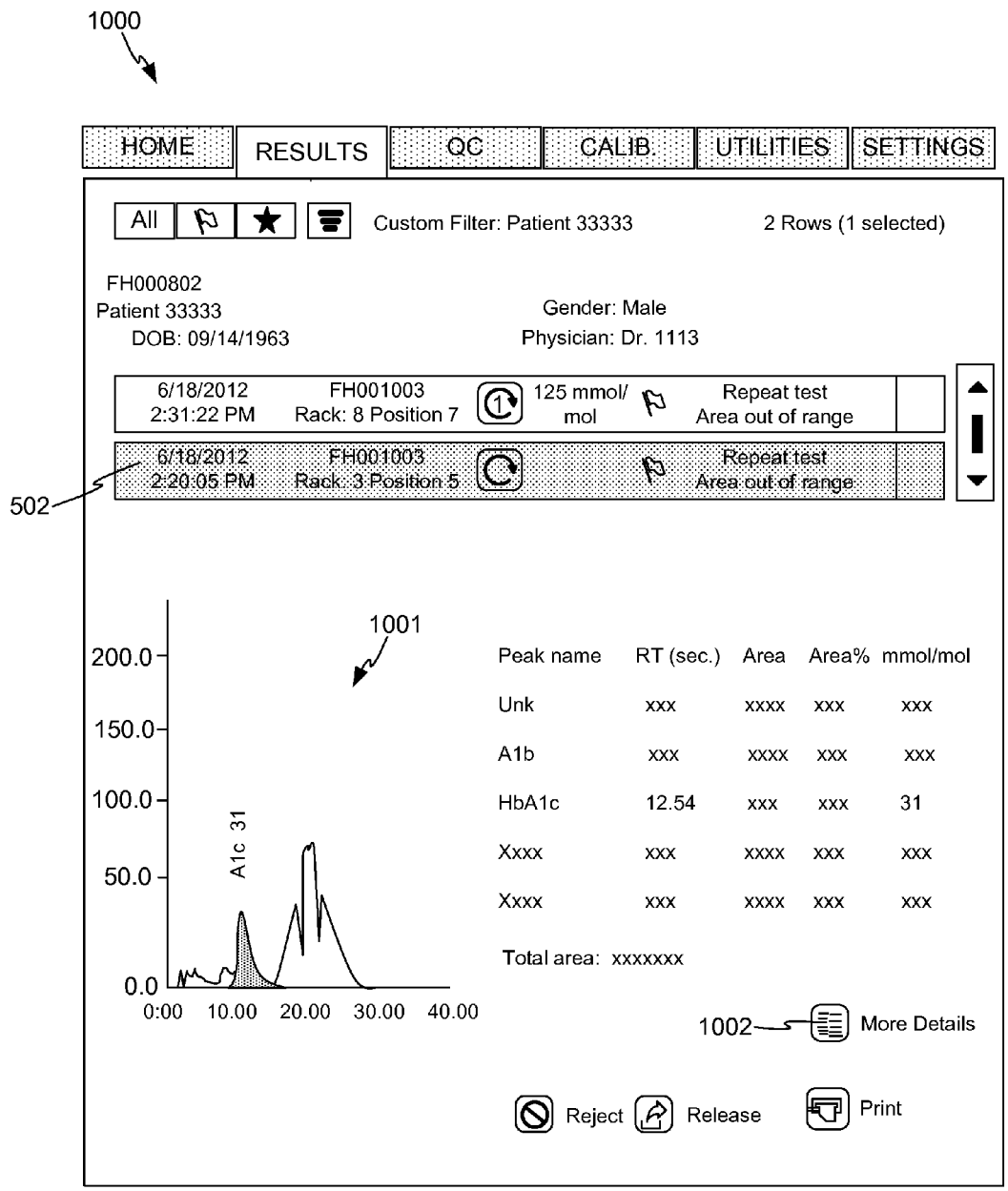
FIG. 10 shows another user interface screen in accordance with embodiments of the invention.

Referring again to FIG. 7, should the user touch icon 704, a user interface screen such as screen 900 shown in FIG. 9 would appear, revealing that test 701 (501) was a repeat of test 502 necessitated by the fact that a problem was detected with test 502. The user can get additional details in a manner similar to getting additional details from a test in user interface screen 500. For example, by tapping twice on test 501 in screen 900, or using some other user interface control, the user can call up a detail screen such as user interface screen 1000 shown in FIG. 10. Screen 1000 reveals that chromatogram 1001 is unusually low in amplitude, such that the integrated area of not only the HbA1c peak but of the entire chromatogram is low. This indicates a possible problem with extraction of the sample, and not merely a low HbA1c reading for the patient.

As before, medical testing machine 100 can provide grouped results and result details because it maintains searchable records of tests it performs. Reports and screens such as those shown in FIGS. 7-10 can be produced quickly and easily, without a laborious search of patient files.

According to another aspect, medical testing machine 100 may provide detail about the state of medical testing machine 100 at the time of any particular test. This capability provides traceability for test results, and may facilitate documentation of laboratory procedures as required by regulation. The level of detail available may be extensive, including calibration records, rules governing repeat testing, batch numbers of consumable items, and other information.

In example user interface screen 1000, a screen location 1002 labeled "More Details" is provided. The user may touch or tap twice on this simulated button to access configuration data and other details indicating the state of testing machine 100 at the time the currently displayed test outcome was obtained (from test 502 in this example).

Figure 11:
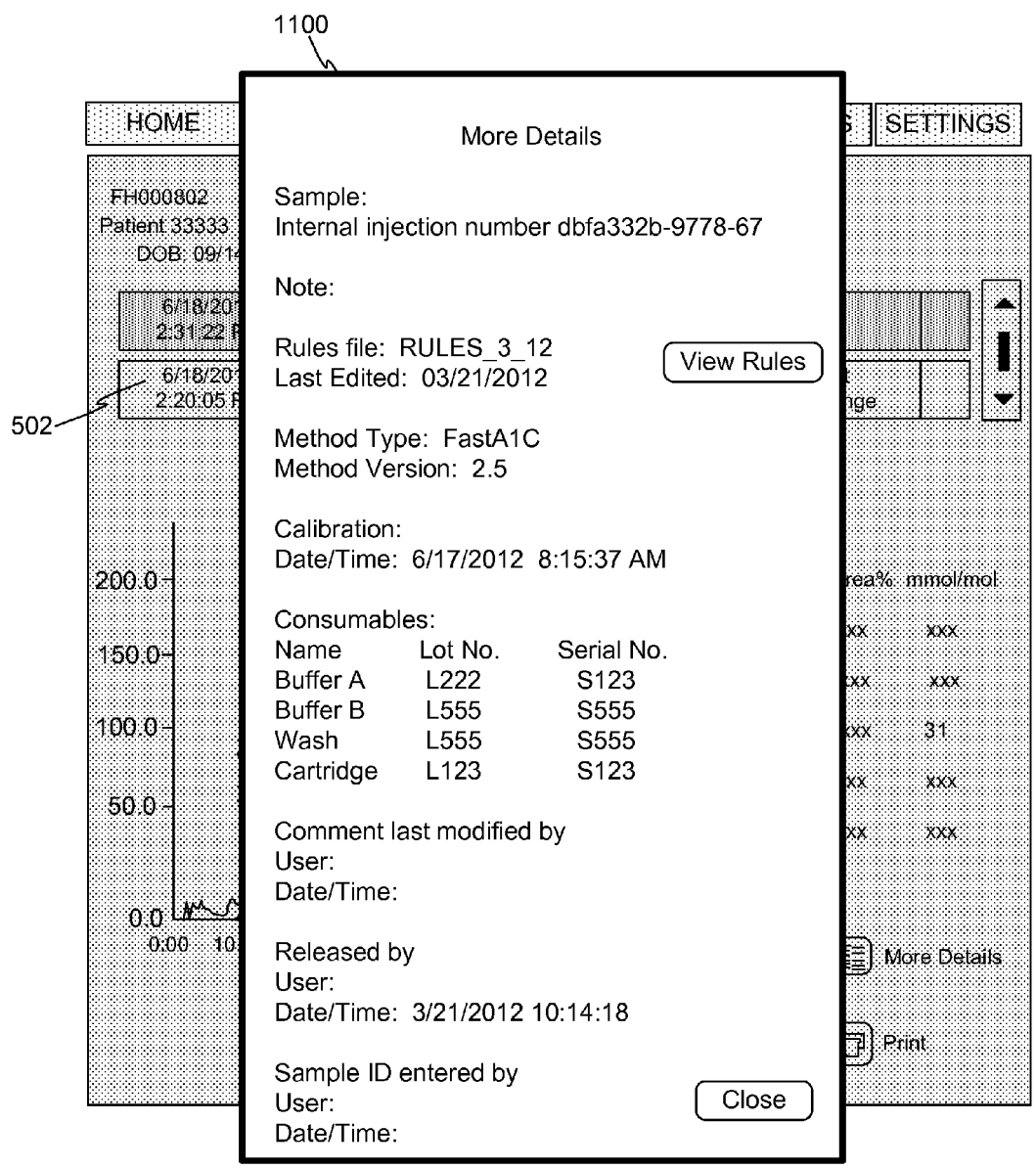
FIG. 11 shows an example user interface window having additional test details, in accordance with embodiments of the invention.

FIG. 11 shows an example user interface window 1100 having additional test details. Other formats and information content may be used. In this example, window 1100 is a pop-up window overlaid on user interface screen 1000, but other kinds of user interface techniques may be used.

Figure 12:
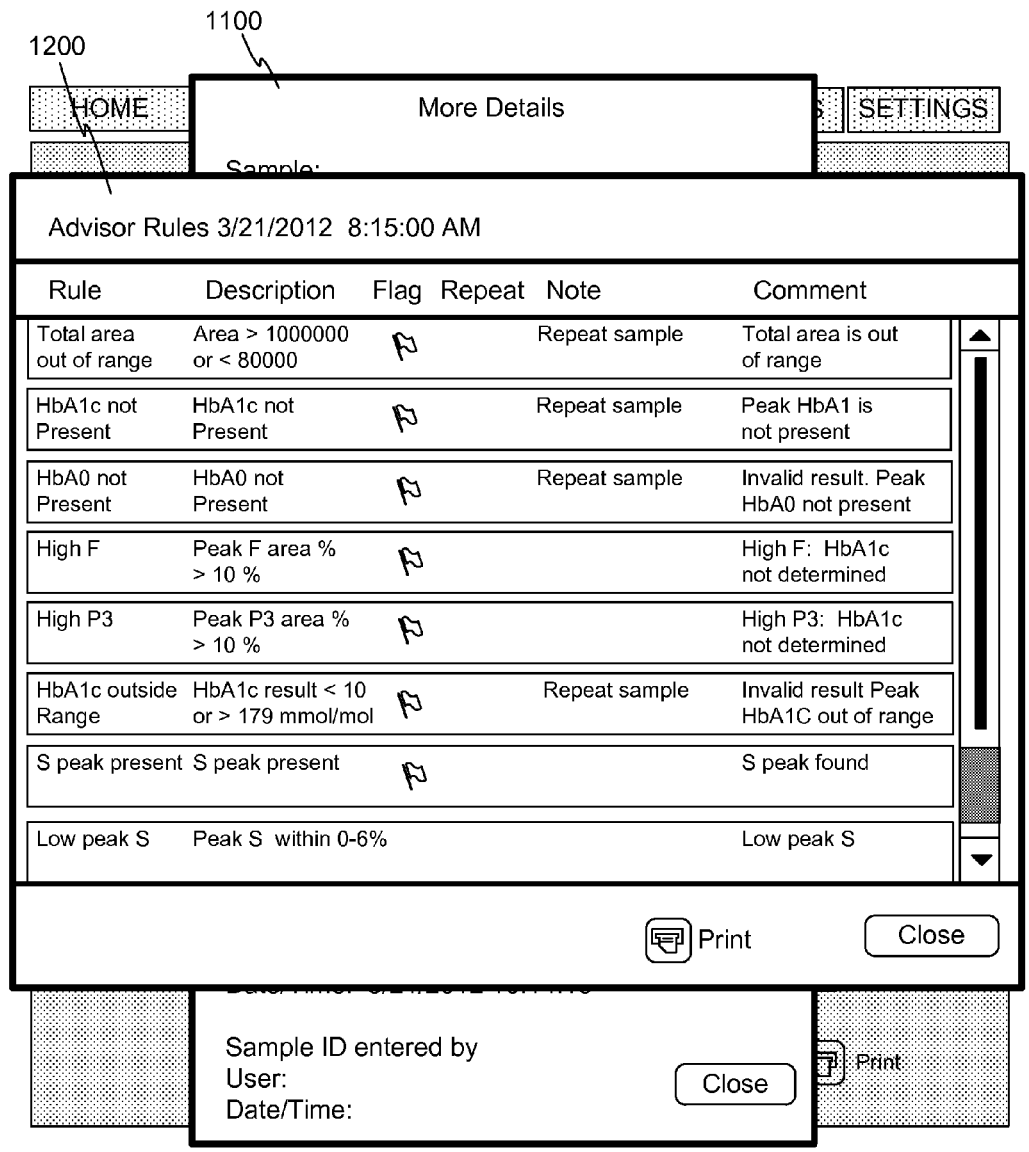
FIG. 12 shows a display of a rules listing, in accordance with embodiments of the invention.

User interface window 1100 also provides a screen location 1101 labeled "View Rules". The user may touch this simulated button to access a listing of the rules that were in place at the time of the test for deciding when retests are necessary and the like. The rules listing may be presented on a user interface screen such as user interface screen 1200 shown in FIG. 12.

Example user interface screen 1200 is a pop-up window overlaid on user interface screen 1000 and window 1100, but other kinds of user interface techniques may be used. Because the rules information is stored and accessed by medical testing machine 100, it can be recalled quickly and easily, without the need to consult calibration logs or other paper documentation. Other user interface screens may enable a user to modify the rule set, and after each modification, subsequent tests are automatically associated with the rule set in place at the time of each test. Similarly, calibrations times are automatically noted and associated with subsequent tests.

According to another aspect, a medical testing machine according to embodiments provides enhanced status information to the user of the machine about the progress of testing. For example, medical testing machine may require as much as 45 to 90 seconds to process each vial. In order to plan his or her activities in the testing lab, a user of medical testing machine 100 may wish to know when a particular test will complete, when medical testing machine 100 will be ready to accept more racks of vials for testing, or other information about the testing status.

Figure 13:
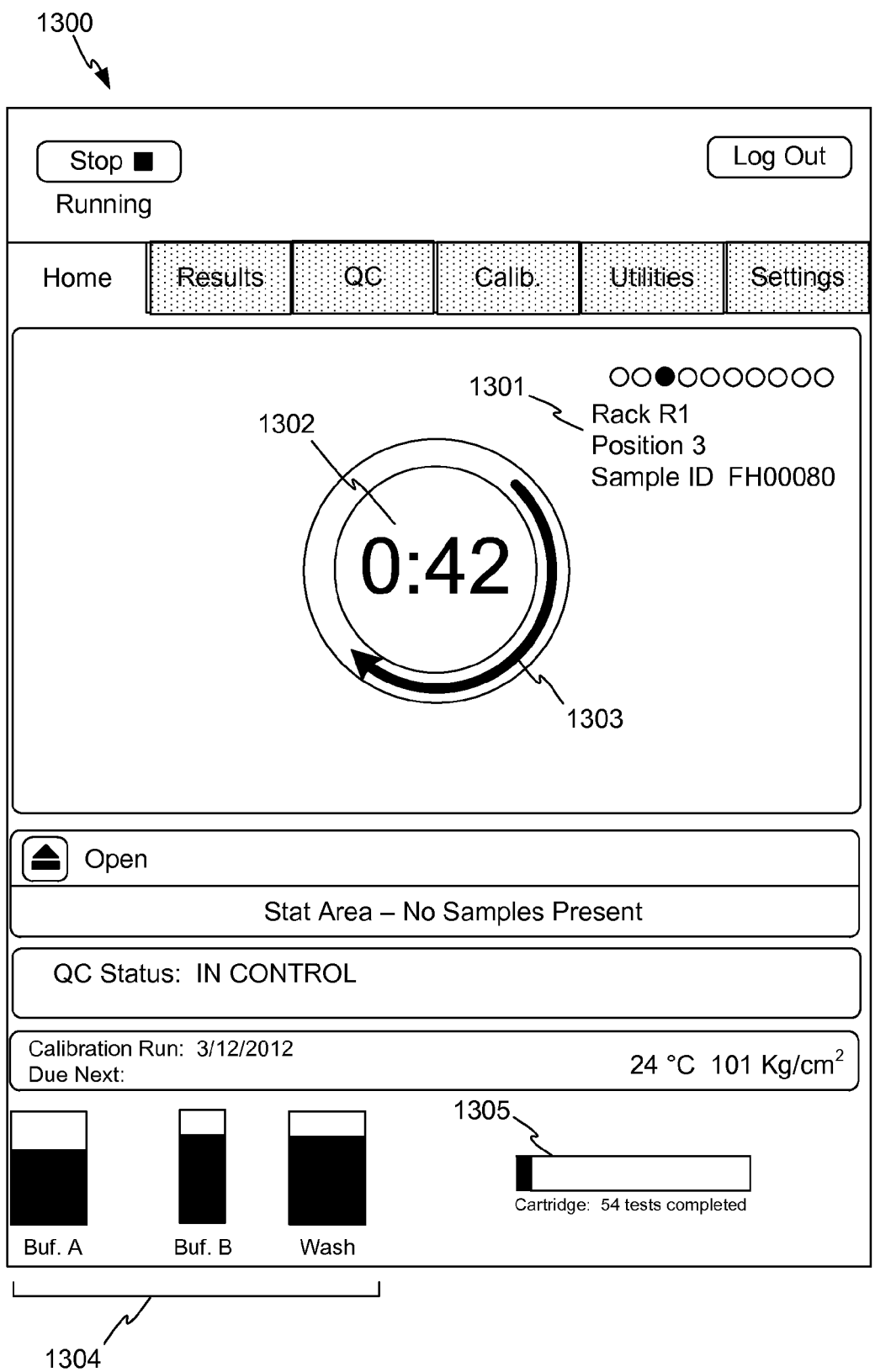
FIG. 13 shows a user interface screen that provides status information, in accordance with embodiments of the invention

FIG. 13 shows a user interface screen 1300 that provides status information, in accordance with embodiments of the invention. User interface screen 1300 may show on display screen 106 while testing is in progress. In example screen 1300, the current rack number and position 1301 of the vial being processed are displayed, enabling the user to quickly determine how long it may be until more samples will need to be loaded into testing machine 100. An animated counter 1302 counts down the time remaining in the test currently underway. An arrow 1303 or shaded feature may rotate around counter 1302 to indicate that testing is progressing. For example, arrow 1303 may rotate about once per second, or at another suitable speed.

User interface screen 1300 also shows at 1304 the current levels of consumable materials remaining in testing machine 100, for example buffers and wash solution, and also indicates at 1305 how much of the expected life of the stationary media has been used.

While embodiments of the invention have been described above in the context of a machine that tests blood for levels of HbA1c hemoglobin using HPLC, it is to be understood that the claims are not so limited, and that the principles of the invention may be embodied in other kinds of testing machines that perform different tests on other fluids, tissue, or other patient media. It is to be understood that all workable combinations of the features and capabilities described herein are also considered to be disclosed. For example, medical testing machine embodying the invention may include any one, any combination, or all of the features and capabilities described above.

The invention may also be embodied in a system or method that operates independently of any particular testing machine. For example, a health care facility may store patient records in electronic form, including the outcomes of tests performed by one or more testing machines. This library of test outcomes can include one or more sets of the test outcomes in which each outcome in a respective set results from testing of the same respective media sample. The facility may use a computerized retrieval system separate from any particular testing machine to retrieve the test outcomes. As in a method performed by the example testing machine discussed above, the system can identify such sets and display the outcomes in each set as a group. The sets may be recognized as having a common accession number, or by other techniques. The test outcomes in a set may displayed as a group regardless of whether one or more of the grouped test outcomes would otherwise be omitted from being displayed by a data filter in place at the time the group display is requested. Such a method may be applied to the outcomes of a test that measures the level of HbA1c hemoglobin in blood, or the outcomes of other tests.

The invention has now been described in detail for the purposes of clarity and understanding. However, it will be appreciated that certain changes and modifications may be practiced within the scope of the appended claims.

What is claimed is:

1. A medical testing machine, comprising:
an input location, an output location, and a vial handling mechanism that moves vials of media sampled from patients from the input location through the testing machine to the output location;
an extraction mechanism that extracts the media from each vial in turn for testing;
a testing system that performs a medical test on the media sampled from patients, each test instance having an outcome, wherein the testing system comprises a high performance liquid chromatography system including a column holding a stationary medium, the high performance liquid chromatography system separating components of the sampled media as the sampled media flows through the column, and the high performance liquid chromatography system including a sensor that senses indications that the separated components are passing the sensor, and wherein the sampled media is blood and the test measures the level of HbA1c hemoglobin in the blood;

a reader that obtains, for each of a plurality of test instances, an identifier of the particular patient from which the media was sampled by reading the identifier from a container that holds the media;

a processor that receives the output of the sensor and determines the outcome for each respective test and that causes test outcomes to be stored in a mass storage memory in association with their respective patient identifiers; and a computerized retrieval system that enables a user to specify a particular patient identifier and cause the computerized retrieval system to retrieve from the mass storage memory test outcomes associated with the particular patient identifier.

2. The medical testing machine of claim 1, further comprising an electronic display on which the retrieved outcomes are shown.

3. The medical testing machine of claim 2, wherein the electronic display is a touchscreen display and also serves as an input device for receiving inputs from the user.

4. The medical testing machine of claim 1, further comprising the mass storage memory.

5. The medical testing machine of claim 1, wherein the mass storage memory is remote from the medical testing machine and is accessible via a computer network.

6. The medical testing machine of claim 1, wherein the reader further obtains for each test instance an accession number of the respective sample.

7. The medical testing machine of claim 6, further comprising a user interface control that causes test outcomes having the same accession number to be shown in a group on the display.

8. The medical testing machine of claim 7, wherein the test outcomes having the same accession number are shown in the group on the electronic display regardless of whether one or more of the grouped test outcomes would otherwise be omitted from being shown on the electronic display by a data filter in place at the time the user interface control is actuated.

9. The medical testing machine of claim 1, wherein the computerized retrieval system enables multiple levels of detail to be shown about each test instance outcome.

10. The medical testing machine of claim 1, wherein the mass storage memory also stores in association with each test instance outcome information about the state of the medical testing machine at the time the particular test instance was run.

11. The medical testing machine of claim 10, wherein the stored state information includes a set of rules used to evaluate test outcomes for validity.

12. The medical testing machine of claim 11, further comprising a user interface control that causes to be displayed, for a particular test instance, the rules in place at the time the particular test instance was run.

13. The medical testing machine of claim 1, further comprising an electronic display, wherein during a particular test instance, an animated counter counts down the time remaining until the test is completed.

14. The medical testing machine of claim 13, wherein the electronic display further shows a rack number and position within the rack of a container from which media was extracted for running the particular test instance.

15. The medical testing machine of claim 13, wherein the electronic display further shows levels of consumable materials remaining in the medical testing machine.

16. A medical testing machine, comprising:

an input location, an output location, and a vial handling mechanism that moves vials of media sampled from patients from the input location through the testing machine to the output location;

an extraction mechanism that extracts the media from each vial in turn for testing;

a testing system that performs a medical test on media sampled from patients, each test instance having an outcome, wherein the testing system comprises a high performance liquid chromatography system including a column holding a stationary medium, the high performance liquid chromatography system separating components of the sampled media as the sampled media flows through the column, and the high performance liquid chromatography system including a sensor that senses indications that the separated components are passing the sensor, and wherein the sampled media is blood and the test measures the level of HbA1c hemoglobin in the blood;

a reader that obtains, for each of a plurality of test instances, an accession number of the particular media sample by reading the accession number from a container that holds the media;

a processor that receives the output of the sensor and determines the outcome for each respective test and that causes each test outcome to be stored in a mass storage memory in association with its respective accession number; and a computerized retrieval system that enables a user to specify a particular accession number and cause the computerized retrieval system to display as a group all of the stored test outcomes having the same accession number.

17. The medical testing machine of claim 16, wherein the test outcomes having the same accession number are displayed as a group regardless of whether one or more of the grouped test outcomes would otherwise be omitted from being displayed by a data filter in place at the time the group display is requested.

18. The medical testing machine of claim 16, wherein the mass storage also stores in association with each test instance outcome information about the state of the medical testing machine at the time the particular test instance was run.

19. The medical testing machine of claim 18, wherein the stored state indication includes a set of rules used to evaluate test outcomes for validity.

20. The medical testing machine of claim 16, further comprising an electronic display, wherein during a particular test instance, an animated counter counts down the time remaining until the test is completed.

21. A medical testing machine, comprising:

an input location, an output location, and a vial handling mechanism that moves vials of media sampled from patients from the input location through the testing machine to the output location;

an extraction mechanism that extracts the media from each vial in turn for testing;

a testing system that performs a medical test on media sampled from patients, each test instance having an outcome, wherein the testing system comprises a high performance liquid chromatography system including a column holding a stationary medium, the high performance liquid chromatography system separating components of the sampled media as the sampled media flows through the column, and the high performance liquid chromatography system including a sensor that senses indications that the separated components are passing the sensor, and wherein the sampled media is blood and the test measures the level of HbA1c hemoglobin in the blood;

a processor that receives the output of the sensor and determines the outcome for each respective test and that causes test outcomes to be stored in a mass storage memory in association with their respective patient identifiers; and a computerized retrieval system that enables a user to specify a particular filter criterion and cause the computerized retrieval system to retrieve from the mass storage memory test outcomes meeting the filter criterion;

wherein the mass storage memory also stores in association with each test instance outcome information about the state of the medical testing machine at the time the particular test instance was run.

22. The medical testing machine of claim 21, wherein the stored state information includes a set of rules used to evaluate test outcomes for validity.

23. The medical testing machine of claim 22, further comprising a user interface control that causes to be displayed, for a particular test instance, the rules in place at the time the particular test instance was run.

24. A method, comprising:
receiving vials of media sampled from patients at an input location of a medical testing machine;
moving the received vials through the medical testing machine to an output location of the medical testing machine;
extracting the media from each vial in turn for testing;
separating components of the sampled media using high performance liquid chromatography, wherein separating the components comprises passing the sampled media through a stationary medium;
sensing the passage of the separated components using a sensor;
recording an outcome of each respective test in a computerized system, wherein the test outcomes result from a test that measures the level of HbA1c hemoglobin in blood;
accessing, using the computerized system, an electronic library of the test outcomes obtained from the performance of the high performance liquid chromatography on the media samples;
identifying in the library one or more sets of the test outcomes in which each outcome in a respective set results from testing of the same respective media sample;
displaying as a group the outcomes in at least one set.

25. The method of claim 24, wherein identifying one or more sets of the test outcomes in which each outcome in a respective set results from testing of the same respective media sample comprises identifying sets of test outcomes having a same accession number.

26. The method of claim 24, wherein the test outcomes in a set are displayed as a group regardless of whether one or more of the grouped test outcomes would otherwise be omitted from being displayed by a data filter in place at the time the group display is requested.

27. The method of claim 24, wherein the library of test outcomes is stored in a testing machine used to perform the medical test.

28. The method of claim 24, wherein the library of test outcomes is stored separately from a testing machine used to perform the medical test.

* * * * *